United States Patent
Mizobuchi et al.

(12)

(10) Patent No.: US 6,299,888 B1
(45) Date of Patent: Oct. 9, 2001

(54) AZELASTINE HYDROCHLORIDE-CONTAINING PERCUTANEOUS PREPARATION HAVING GOOD PERCUTANEOUS ABSORBABILITY AND REDUCED SKIN IRRITATION

(75) Inventors: Noriko Mizobuchi, Kagawa-ken; Sayuri Seto, Tokyo-to, both of (JP)

(73) Assignee: Teikoku Seiyaku Kabushiki Kaisha, Ookawa-gun (JP)

( * ) Notice: Subject to any disclaimer, the term of this patent is extended or adjusted under 35 U.S.C. 154(b) by 0 days.

(21) Appl. No.: 09/147,747

(22) PCT Filed: Jun. 29, 1998

(86) PCT No.: PCT/JP98/02953

§ 371 Date: Mar. 1, 1999

§ 102(e) Date: Mar. 1, 1999

(87) PCT Pub. No.: WO99/01137

PCT Pub. Date: Jan. 14, 1999

(30) Foreign Application Priority Data

Jul. 2, 1997 (JP) .................................................. 9-177242

(51) Int. Cl.[7] ............................. A61K 7/00; A61K 31/55
(52) U.S. Cl. ........................................... 424/401; 514/212
(58) Field of Search .............................. 514/212; 424/401

(56) References Cited

U.S. PATENT DOCUMENTS

| 5,110,814 | * | 5/1992 | Engel et al. ........................ 514/212 |
| 5,164,194 | * | 11/1992 | Hettche ................................ 424/489 |
| 5,176,916 | * | 1/1993 | Yamanaka et al. .................. 424/448 |

FOREIGN PATENT DOCUMENTS

| 0 316 633 | 5/1989 | (EP) . |
| 0 338 444 | 10/1989 | (EP) . |
| 0 378 086 | 7/1990 | (EP) . |
| 0 396 069 | 11/1990 | (EP) . |
| 2-124824 A | * 5/1990 | (JP) . |
| 6-40949 A | * 2/1994 | (JP) . |

OTHER PUBLICATIONS

Dermatological Preparations of Nowadays, edited by Masahiko Takano, 1982, pp. 163–183, 263–275, 345–348, 358.*

* cited by examiner

*Primary Examiner*—Thurman K. Page
*Assistant Examiner*—Amy E Pulliam
(74) *Attorney, Agent, or Firm*—Oblon, Spivak, McClelland, Maier & Neustadt, P.C.

(57) ABSTRACT

The invention relates to azelastine hydrochloride-containing percutaneous preparations which comprises, as base ingredients;
  hydrocarbon and/or beeswax, and
  a surfactant.

5 Claims, No Drawings

AZELASTINE HYDROCHLORIDE-CONTAINING PERCUTANEOUS PREPARATION HAVING GOOD PERCUTANEOUS ABSORBABILITY AND REDUCED SKIN IRRITATION

TECHNICAL FIELD

The present invention relates to pharmaceutical preparations which contain azelastine hydrochloride as the pharmaceutically active ingredient but cause markedly little irritation to the skin.

PRIOR ART

Azelastine hydrochloride is widely being used as an anti-allergic agent mainly in the form of oral preparations in the treatment of diseases such as bronchial asthma, urticaria, and pruritus. In general the skin permeability of a basic drug is said to be high when the drug is in the undissociated form and low when the drug is in the dissociated form. Azelastine hydrochloride, as a basic drug, is thought to show better absorption at higher pHs at which the drug exists as undissociated molecules. However, because the dissociation constant (pKa) is as high as about 9.5, the pH of the pharmaceutical preparation needs to be about pH 9.5 so that the fraction of undissociated molecules may be 50% to ensure good skin permeability. However, such a pH is far higher than the physiological pH of the skin, mucosa, etc. That is, a pharmaceutical preparation having such a high pH is very irritative to the skin, possibly causing skin lesions. To lower the pH, an addition of a pH-adjusting agent may be an option, but at a low pH, most of the azelastine hydrochloride molecules exist in the dissociated form, so that addition of a large amount of such a pH-adjusting agent may decrease absorption. In addition, when the pH is below 4, the acidic conditions may cause skin lesions. Therefore addition of a pH-adjusting agent is not recommended.

Various investigations have been conducted on base ingredients that can enhance the absorption of azelastine hydrochloride within a physiologically acceptable pH range.

For example, the Japanese Unexamined Patent Publication No. Hei 2-124824 disclosed preparations containing monoglycerides of fatty acids having 8 to 12 carbon atoms and/or lactic acid esters of aliphatic alcohol having 12 to 18 carbon atoms, and the Japanese Unexamined Patent Publication No.Hei 6-40949 disclosed preparations containing fatty acids having 8 or more carbon atoms.

However, the additives used in the preparations disclosed in the above-mentioned publications are very irritative to the skin. Therefore there arises a new concern regarding the skin irritation of the additive itself, even though the percutaneous preparation combined with such an additive can solve the problem of skin lesions due to the high pH.

DISCLOSURE OF THE INVENTION

The present invention has been developed with such considerations in mind and its purpose is to provide an azelastine hydrochloride-containing preparation with low skin irritation and excellent percutaneous absorbability of azelastine hydrochloride, the pharmaceutically active ingredient.

In essence, an azelastine hydrochloride-containing percutaneous preparation of the present invention to be solved the above problems comprises ① hydrocarbons and/or beeswax, ② higher alcohols and/or polyhydric alcohols, and ③ a surfactant.

BEST MODE FOR CARRYING OUT THE INVENTION

As described above, some methods have been disclosed to improve the skin permeability of azelastine hydrochloride without increasing the pH of the preparation, but these methods were unsatisfactory because they do not sufficiently consider the issue of reducing irritation to the skin. For example, the Japanese Unexamined Publication Patent Application No.Hei 6-40949 describes that "a fatty acid having 8 or more carbon atoms" added as an essential ingredient was selected as an additive with low irritation and high safety. However, some of the above fatty acids are high irritative to skin even when used alone according to an experiment by the present inventors. Thus it was found that the problem of the irritation of the preparations was not much solved and moreover the irritation persisted long after application.

Thus the skin irritation of azelastine hydrochloride-containing percutaneous pharmaceutical preparations had long been known, but had not been studied as the primary problem to be solved, and therefore the problem regarding the above skin irritation has not been solved to date. One of the main purpose in the present invention is to improve irritation to the skin, and another purpose of the present invention is to provide a preparation excellent in percutaneous absorbability of azelastine hydrochloride. For the above purposes, the present inventors have studied, as a result, they found that use of the above-mentioned base ingredients in the specified combination could achieve their purposes, and the present invention came about as a result of their research.

The fundamental concept of the present invention consists in the use of base ingredients prepared by appropriately combining only additives with low irritation, thereby to reduce not only the irritation due to the additives but also the irritation of the preparation as a whole, and at the same time to enhance the skin permeability of azelastine hydrochloride at a physiologically acceptable pH which will not cause skin lesions.

First the base ingredients which characterize the present invention are explained.

① Hydrocarbons and/or Beeswax

These are frequently used as oily bases, being non-irritative and stable.

The hydrocarbons include saturated hydrocarbons represented by $C_nH_{2n+2}$ [e.g. petrolatum (white petrolatum, yellow petrolatum, etc.), liquid paraffin, paraffin, etc.], materials containing a hydrocarbon as a major ingredient [e.g. gelatinized hydrocarbons prepared by dissolution of polyethylene resin in liquid paraffin by heating [Trade name "Plasty Base" (E. R. Squibb & Sons)], and waxes (microcrystalline wax, paraffin wax, etc.)]. Among them yellow petrolatum, white petrolatum, and gelatinized hydrocarbons are desirable.

Beeswax contains esters of higher fatty acids and higher monohydric alcohol as a major ingredient, including yellow beeswax and white beeswax, of which white beeswax is recommended.

These materials may be used alone or in combination of two or more.

The total content of the above-mentioned hydrocarbons and beeswax is preferable 10 to 97% of the whole amount of the preparation. When the content is below 10%, it is difficult for the preparation to maintain a semi-solid state; for example, creams may be separated into the solid phase and the aqueous phase, it is impossible to keep the preparation stable. The content is more preferable not less than 15%, and furthermore preferable not less than 20%. When the content is above 97%, it is impossible to add enough water to dissolve azelastine hydrochloride. As a result, their crystals is precipitated in the preparation, and the dispersion of the active ingredient is poor. The content is more preferable not be more than 95%, furthermore preferable not be more desirably not more than 90%.

② Higher Alcohols and/or Polyhydric Alcohols

The above-mentioned higher alcohols are preferable saturated or unsaturated alcohols having 12 to 18 carbon atoms, such as aliphatic saturated alcohols [dodecanol (lauryl alcohol) (C=12), myristyl alcohol (C=14), cetanol (palmityl alcohol) (C=16), cetostearyl alcohol (mixture of cetanol and stearyl alcohol in equal amounts), stearyl alcohol (C=18), etc.], and aliphatic unsaturated alcohols [oleyl alcohol (C=18), etc.] and the like. Among these, cetanol, cetostearyl alcohol, and stearyl alcohol are recommended.

The above-mentioned polyhydric alcohols include those having 2 or more carbon atoms such as ethylene glycol, propylene glycol, dipropylene glycol, polyethylene glycol, glycerol, sorbitol, etc. Among these, propylene glycol and polyethylene glycol are recommended.

These alcohols may be used alone or in combination of two or more.

The total content of the above-described higher alcohols and/or polyhydric alcohols is preferable 0.5 to 35% of the amount of the whole preparation. When the content is below 0.5%, the balance between the aqueous phase and the oily phase of a cream is lost so that it is difficult to prepare a cream. The content is more preferable not less than 1%, and furthermore preferable not less than 2%. When the content is above 35%, the preparation becomes hard, which makes application to the skin difficult. The content is more preferable not more than 30%, and furthermore preferable not more than 25%.

③ Surfactants

Surfactants that are used in the present invention include non-ionic surfactants [fatty acid-polyhydric alcohol esters (e.g. glycerol monostearate, sorbitan monooleate, sucrose-fatty acid esters, cholesterol, etc.), polyoxyalkylene fatty acid-polyhydric alcohol (e.g. polyoxyethylene coconut oil fatty acid sorbitan, etc.), fatty acid-polyoxyalkylene polyhydric alcohol esters (e.g. poly(oxyethylene)sorbitol monooleate, etc.), fatty acid-poly(alkylene glycol)esters (e.g. poly(oxyethylene glycol)monooleate, poly(ethylene glycol)dioleate, etc.), alkyl ethers of polyhydric alcohols (e.g. isostearyl glyceryl ether, etc.), polyoxyalkylene alkyl ethers (e.g. polyoxyethylene lauryl alcohol ether, polyoxyethylene stearyl ether, etc.)], anionic surfactants (sodium dodecylsulfate, sodium alkylbenzenesulfonate, etc.), and cationic surfactants (benzalconium chloride, etc.). Among these, polyoxyethylene hydrogenated caster oil, polyoxyethylene lauryl alcohol ether, glycerol monostearate, and cholesterol are recommended.

These may be used alone or in combination of two or more.

The total content of the above-mentioned surfactants is preferable 0.5 to 10% of the amount of the whole preparation. When the content is below 0.5%, the preparation becomes too hard to be applied to the skin. The content is more preferable not less than 1% and furthermore preferable not less than 1.5%. When the content is above 10%, the preparation is apt to cause skin irritation and loses its appropriate hardness to become sticky. The content is more preferable not more than 8% and furthermore preferable not more than 6%.

The base ingredients used in the invention contains the above-mentioned ingredients as the essential components and does not contain any other irritative additive (e.g. fatty acids, etc.). In this sense the present invention is different from that disclosed in the Japanese Unexamined Patent Publication No.Hei 6-40949 which contains fatty acids as the essential component. In addition, the present invention differs from the above Publication in the problems to be solved. Therefore, these should be discriminated distinctly from each other.

The pharmaceutical preparation of the present invention may additionally contain a pH-adjusting agent for adjustment of the pH of the preparation (e.g. sodium hydroxide, sodium carbonate, sodium bicarbonate, etc.), an additive usually used for production of pharmaceutical preparations [for example, a preservative (e.g. p-hydroxybenzoic acid ester, thymol, benzoic acid, salicylic acid, etc.), an antioxidant (e.g. dibutylhydroxytoluene, tocopherol, etc.), a flavoring agent (e.g. l-menthol, dl-camphur, etc.), a colorant (e.g. synthetic organic food additives, annatto pigment, etc.) and the like, as needed.

In the preparation of the present invention, the content of azelastine hydrochloride as the pharmaceutically active ingredient is preferable 0.001 to 5% of the whole amount of the preparation. When the content is below 0.001%, the pharmacological effect is insufficient. The content is more preferable not less than 0.005%, and furthermore preferable not less than 2%. When the content is above 5%, it is difficult to uniformly dissolve or disperse the azelastine hydrochloride in the preparation. The content is more preferable not more than 3%, and furthermore preferable not more than 2%.

The form of the preparation of the present invention is not limited as far as it is a form suitable for percutaneous absorbability, for example, it may be a liquid preparation such as eye drops, nasal drops, lotions, syrups, sprays, and the like; a semi-solid preparation such as ointments, creams, gels, tapes, cataplasms, and the like; or a solid preparation such as suppositories, and the like.

For production of the preparation in a desired form, ingredients usually used as the starting materials for pharmaceutical preparations may be adequately combined in addition to the above-mentioned essential ingredients. Some Preparation Examples are concretely described below.

The present invention is explained in more detail by the Examples. The Examples described below do not restrict the invention at all, and it is within the technical scope of the invention that the invention is modified in its working within the range compatible with the purport of the invention as described above or below.

PREPARATION EXAMPLE 1

[Preparation of a Hydrophilic Ointment (1)]

| Ingredient | Amount to be blended |
|---|---|
| azelastine hydrochloride | 0.3 g |
| white petrolatum | q.s. |
| polyoxyethylene lauryl ether | 5.0 g |
| propylene glycol | 2.5 g |
| 8N sodium hydroxide | 0.01 g |
| purified water | 2.5 g |
| | To make 100 g |

First, azelastine hydrochloride was added into a mixture of purified water and propylene glycol, and dissolved by heating at 80° C. Separately, white petrolatum and polyoxyethylene lauryl ether were mixed and dissolveed by heating at 80° C. To the dissolveed mixture was added the above-mentioned azelastine hydrochloride solution, followed by mixing them in a vacuum emulsifier. Then the pH of the resulted preparation was adjusted to about 7 at 35° C. with 8N sodium hydroxide.

To this resultant solution, white petrolatum was added to mix uniformly, and adjusted to make a total weight of 100 g. This was followed by cooling, and gave a hydrophilic petrolatum ointment containing 0.3% of azelastine hydrochloride.

PREPARATION EXAMPLE 2
[Preparation of a Hydrophilic Ointment (2)]

| Ingredient | Amount to be blended |
| --- | --- |
| azelastine hydrochloride | 0.1 g |
| gelatinized hydrocarbon | q.s. |
| polyoxyethylene lauryl ether | 5.0 g |
| macrogol 600 | 2.5 g |
| 8N sodium hydroxide | 0.005 g |
| purified water | 2.5 g |
|  | To make 100 g |

First, azelastine hydrochloride was added into a mixture of purified water and macrogol 600 (polyethylene glycol 600), and dissolved by heating at 80° C. Separately, gelatinized hydrocarbon and polyoxyethylene lauryl ether were mixed. To the mixture was added the above-mentioned azelastine hydrochloride solution, and this was followed by mixing in a kneader. Then the pH of the resulting preparation was adjusted to about 7 at 35° C. with 8N sodium hydroxide. To this resultant solution, gelatinized hydrocarbon was added to mix uniformly, and adjusted to make a total weight of 100 g. The mixture was then cooled and gave an ointment containing 0.1% of azelastine hydrochloride.

PREPARATION EXAMPLE 3
[Preparation of a Hydrophilic Ointment (3)]

| Ingredient | Amount to be blended |
| --- | --- |
| azelastine hydrochloride | 0.001 g |
| white petrolatum | q.s. |
| white beeswax | 8.0 g |
| cholesterol | 3.0 g |
| stearyl alcohol | 3.0 g |
| 8N sodium hydroxide | trace |
| purified water | 5.0 g |
|  | To make 100 g |

First, azelastine hydrochloride was added into purified water, and dissolved by heating at 80° C. Separately, white petrolatum, white beeswax, cholesterol and stearyl alcohol were dissolveed together by heating at 80° C. To the dissolveed mixture was added the above-mentioned azelastine hydrochloride solution, and the resultant mixture was mixed in a vacuum emulsifier by heating at 80° C. Then the pH of the resultant preparation was adjusted to about 7 at 35° C. with 8N sodium hydroxide. To this resultant solution, white petrolatum was added to mix uniformly, and adjusted to make a total weight of 100 g. This was followed by cooling, and gave an ointment containing 0.001% of azelastine hydrochloride.

PREPARATION EXAMPLE 4
[Preparation of a Hydrophilic Ointment (4)]

| Ingredient | Amount to be blended |
| --- | --- |
| azelastine hydrochloride | 2.0 g |
| white petrolatum | q.s. |
| white beeswax | 8.0 g |
| cholesterol | 3.0 g |
| cetostearyl alcohol | 3.0 g |
| 8N sodium hydroxide | 0.05 g |
| purified water | 5.0 g |
|  | To make 100 g |

This Preparation Example was conducted in similar to Preparation Example 3 except that cetostearyl alcohol was used in place of stearyl alcohol to give an ointment containing 2% of azelastine hydrochloride.

PREPARATION EXAMPLE 5
[Preparation of a Hydrophilic Ointment (5)]

| Ingredient | Amount to be blended |
| --- | --- |
| azelastine hydrochloride | 0.5 g |
| white petrolatum | q.s. |
| white beeswax | 8.0 g |
| cholesterol | 3.0 g |
| stearyl alcohol | 1.5 g |
| cetanol | 1.5 g |
| 8N sodium hydroxide | 0.015 g |
| purified water | 5.0 g |
|  | To make 100 g |

This Preparation Example was conducted in similar to Preparation Example 3 except that a 1:1 mixture of stearyl alcohol and cetanol was used in place of only stearyl alcohol to give an ointment containing 0.5% of azelastine hydrochloride.

PREPARATION EXAMPLE 6
[Preparation of a Cream (1)]

| Ingredient | Amount to be blended |
| --- | --- |
| azelastine hydrochloride | 5.0 g |
| white petrolatum | 35.0 g |
| polyoxyethylene hydrogenated castor oil | 4.0 g |
| glycerol monostearate | 1.0 g |
| cetanol | 10.0 g |
| propylene glycol | 10.0 g |
| 8N sodium hydroxide | 1.6 g |
| purified water | q.s. |
|  | To make 100 g |

First, azelastine hydrochloride was added to purified water, and dissolved by heating at 80° C. Separately, white petrolatum, polyoxyethylene hydrogenated castor oil, glycerol monostearate, and cetanol were dissolveed together by heating at 80° C. To the resultant mixture were added the above-mentioned azelastine hydrochloride solution and propylene glycol, and mixed in a vacuum emulsifier. The pH of the resulting preparation was then adjusted to about 7 at 35° C. with 8N sodium hydroxide. To this resultant solution was added purified water to make a total weight of 100 g, followed by mixing and emulsifying, to give a cream containing 5% of azelastine hydrochloride.

PREPARATION EXAMPLE 7
[Preparation of a Cream (2)]

| Ingredient | Amount to be blended |
|---|---|
| azelastine hydrochloride | 0.3 g |
| white petrolatum | 20.0 g |
| yellow petrolatum | 15.0 g |
| polyoxyethylene hydrogenated castor oil | 4.0 g |
| glycerol monostearate | 1.0 g |
| stearyl alcohol | 10.0 g |
| methyl p-hydroxybenzoate | 0.1 g |
| propyl p-hydroxybenzoate | 0.1 g |
| propylene glycol | 10.0 g |
| 8N sodium hydroxide | 0.11 g |
| purified water | q.s. |
| | To make 100 g |

First, azelastine hydrochloride was added to purified water, and dissolved by heating at 80° C. Separately, white petrolatum, yellow petrolatum, polyoxyethylene hydrogenated castor oil, glycerol monostearate, and stearyl alcohol were dissolveed together by heating at 80° C. To the resulting mixture was added the above-mentioned azelastine hydrochloride solution, followed by mixing in a vacuum emulsifier. To the resultant mixture was added a solution of methyl p-hydroxybenzoate and propyl p-hydroxybenzoate in propylene glycol to mix, and emulsified. The pH of the resulting preparation was then adjusted to about 7 at 35° C. with 8N sodium hydroxide. To the solution was added purified water to make a total weight of 100 g, followed by further mixing and emulsifying, to give a cream containing 0.3% of azelastine hydrochloride.

Comparative Preparation 1
[Preparation of an Ointment (1)]

| Ingredient | Amount to be blended |
|---|---|
| azelastine hydrochloride | 0.3 g |
| glycerol monooleate | 9.0 g |
| gelatinized hydrocarbon | q.s. |
| dipropylene glycol | 6.0 g |
| 8N sodium hydroxide | 0.01 g |
| lauric acid | 0.3 g |
| | To make 100 g |

Prescribed amounts of azelastine hydrochloride, oleic acid, dipropylene glycol and glycerol monooleate were heated and dissolved. Then gelatinized hydrocarbon was added and mixed in a kneader. To the resultant mixture was added 8N sodium hydroxide to adjust the pH of the preparation to about 7 at 35° C. Gelatinized hydrocarbon was then added and mixed uniformly to make a total weight of 100 g. The resultant mixture was followed by cooling, and gave an ointment containing 0.3% of azelastine hydrochloride.

Comparative Preparation 2
[Preparation of an Ointment (2)]

| Ingredient | Amount to be blended |
|---|---|
| azelastine hydrochloride | 0.3 g |
| carboxyvinyl polymer | 0.6 g |
| lecithin | 0.2 g |
| propylene glycol | 5.0 g |
| ethanol | 5.0 g |
| 8N sodium hydroxide | 0.14 g |
| purified water | q.s. |
| oleic acid | 0.5 g |
| | To make 100 g |

Prescribed amounts of azelastine hydrochloride, oleic acid, and lecithin were added to the mixture of propylene glycol and ethanol, and dissolved. Separately, carboxyvinyl polymer was dissolved in purified water which was then gelatinized. To the resulting gel was added the above-mentioned azelastine hydrochloride solution, followed by stirring. The pH of the resultant preparation was adjusted to about 7 at 35° C. with the 8N sodium hydroxide. Then purified water was added to make a total weight of 100 g, which was then stirred to make the preparation uniformly, and gave a gel ointment containing 0.3% of azelastine hydrochloride.

Working Example 1

(A Test for Inhibition of Histamine-induced Increase of Vascular Permeability in Rats)

Tests for inhibition of histamine-induced increase of vascular permeability in rats were performed according to the procedure described below where the preparations obtained by Preparation Example 1 and Comparative Preparation Example 1 were used in the test groups. A control group was given none of the preparations. Each of the test groups and control group were used 10 Wistar rats weighing 400 to 450 g each.

Hair at the back of the rat was removed, and 0.05 g each of the above-mentioned preparations was applied to the site intended for injection of a prophlogistic agent (=histamine). One hour after the first application, a second application was conducted in a similar manner to the first, and 0.2% solution of histamine in physiological saline was injected intracutaneously as a prophlogistic agent at 1 hour after the second application (0.05 mL/site). Immediately after the intracutaneous injection, 1% solution of Evans blue in physiological saline was administered intravenously (0.8 to 0.9 mL/animal), and then the rat was killed and its skin was obtained. The large diameter and small diamater of the area stained blue by Evans blue were measured with calipers. The product of those measurements represented the blue-stained area.

In the control group, the rats were treated similarly to those in the test groups except that no preparation was applied, and the Evans blue-stained area was calculated.

The rate of suppression of vascular permeability for each preparation was calculated according to the following equation.

Rate of suppression of histamine-induced vascular permeability (%)=[blue-stained area in the test group/blue-stained area in the control group]×100

The results are shown in Table 1.

TABLE 1

|  | Preparation Example 1 | Comparative Preparation Example 1 |
|---|---|---|
| rate of suppression of histamine-induced vascular permeability (%) | 26.84 ± 4.84 | 24.30 ± 5.37 |

As seen from Table 1, the rate of suppression of histamine-induced vascular permeability was roughly the same for the two preparations. Thus it was found that the Preparation Example 1 of the present invention had excellent percutaneous absorbability, giving the pharmaceutical effect of azelastine hydrochloride sufficiently.

Working Example 2
(In vitro Skin Permeability Test)

In vitro tests for skin permeability were performed according to the procedure described below where 10 rats were used for each of the preparations obtained by Preparation Examples 1 and 7, and Comparative Preparation Example 1.

Hair of the abdominal area of the Wistar rat (male, 6-week-old) was removed with a clipper and a shaver. The skin sample was then removed, and placed with the epithelium side up in the Franz diffusion cell (effective permeation area of 1.77 $cm^2$, receiver capacity of 10 mL). Physiological saline was used as the receiver solution. After application of 100 mg of the preparation on the epithelium, the receiver solution was stirred with a magnetic stirrer on a water bath at 32° C. After 24 hours of stirring, the receiver solution was sampled to determine the concentration of azelastine in the solution as an amount of azelastine hydrochloride ($\mu$g) by high performance liquid chromatography.

The skin permeability of each preparation was calculated by the following equation.

Skin permeability (%)=(amount of azelastine hydrochloride permeated through the skin)/(amount of azelastine hydrochloride in the preparation (100 mg))×100

The results are summarized in Table 2.

TABLE 2

|  | Amount of the azelastine hydrochloride ($\mu$g) | skin permeability (%) |
|---|---|---|
| Preparation Example 1 | 140 | 47 |
| Preparation Example 7 | 214 | 71 |
| Comparative Preparation Example 1 | 152 | 51 |

As seen from Table 2, each of the preparations of the present invention had permeability equivalent to or higher than that with the preparation obtained by the Comparative Preparation Example 1, indicating that the preparations of the present invention show excellent release of the active ingredient.

Working Example 3
(Skin Irritation Test)

Skin irritation tests were performed on 5 subjects (A to E) according to the procedure described below where the preparations obtained by Preparation Examples 1 and 7 and Comparative Preparation Examples 1 and 2 were used.

Twenty mg of each preparation was applied on the arm of the subjects by using the Finn chamber, and a protecting cover was placed on the arm. The protecting cover was removed after 24 hours, and the symptoms on the skin were evaluated visually at 1, 24, and 48 hours after removal of the cover. The following criteria were used for scoring.

score 2: Irritation was observed all over the skin (severe irritation).
score 1: Irritation was observed sporadically (moderate irritation).
score 0: No irritation was observed (no irritation).

The results are summarized in Table 3.

TABLE 3

|  |  | A | B | C | D | E | Total | mean |
|---|---|---|---|---|---|---|---|---|
| Preparation Example 1 | 1 hr | 0 | +1 | +2 | +2 | 0 | 5 | 1 |
|  | 24 hr | 0 | 0 | 0 | 0 | 0 | 0 | 0 |
|  | 48 hr | 0 | 0 | 0 | 0 | 0 | 0 | 0 |
| Preparation Example 7 | 1 hr | 0 | +1 | +1 | +1 | 0 | 3 | 0.6 |
|  | 24 hr | 0 | 0 | +1 | 0 | 0 | 1 | 0.2 |
|  | 48 hr | 0 | 0 | 0 | 0 | 0 | 0 | 0 |
| Comparative Preparation Example 1 | 1 hr | +2 | +2 | +2 | +2 | 0 | 8 | 1.6 |
|  | 24 hr | 0 | +1 | 0 | 0 | 0 | 1 | 0.2 |
|  | 48 hr | 0 | +2 | 0 | 0 | 0 | 2 | 0.4 |
| Comparative Preparation Example 2 | 1 hr | 0 | +2 | +2 | +2 | +1 | 7 | 1.4 |
|  | 24 hr | 0 | +2 | 0 | +1 | 0 | 3 | 0.6 |
|  | 48 hr | 0 | +2 | 0 | +1 | 0 | 3 | 0.6 |

The preparations of the present invention caused moderate or more intensive irritation in about a half of the subjects (in 6 out of 10 cases) at 1 hour after removal, however, such an irritaioned had disappeared in most cases by 24 hours after removel (observed only in 1 out of 10 cases) and no irritation was observed at 48 hours after removal (0 out of 10 cases).

In contrast, the preparations obtained by Comparative Preparations Example 1 or 2 caused as follows:at 1 hour after removal, 3 or 4 out of 5 cases had severe irritation; at 24 hours after removal, 1 case still remained severe irritation and 2 cases had moderate irritation; at 48 hours after removal, the number of case with irritation increased to 2 cases, and 1 case had more irritation.

Thus the preparations of the present invention caused relatively mild irritation, if any, which disappeared in a short time, whereas the preparations obtained by the Comparative Preparation Examples caused more severe irritation which persisted for a long time and disappeared with difficulty. Thus it was demonstrated that the preparation of the present invention is able to reduce skin irritation markedly, allowing irritation to disappear rapidly.

Industrial Applicability

The preparation of the present invention, being composed as described above, shows reduced skin irritation and the rapid disappearance of irritation when it occurs. In addition, the preparation of the present invention gives the pharmacological effect of azelastine hydrochloride sufficiently, being excellent percutaneous absorbability.

What is claimed is:

1. A percutaneous preparation which comprises:
   0.001 to 5 weight % of azelastine hydrochloride;
   10 to 97 weight % of at least one hydrocarbon and/or beeswax, wherein said hydrocarbon is selected from the group consisting of white petrolatum, yellow petrolatum, and gelatinized hydrocarbon;
   0.5 to 35 weight % of at least one higher alcohol and/or polyhydric alcohol, wherein said higher alcohol is selected from the group consisting of stearyl alcohol, cetanol, and cetostearyl alcohol, and wherein said polyhydric alcohol is selected from the group consisting of propylene glycol and polyethylene glycol; and 0.5 to 10 weight % of at least one surfactant selected from the group consisting of polyoxyethylene hydrogenated castor oil, glycerol monostearate, polyoxyethylene lauryl ether, and cholesterol; and wherein said composition does not contain a fatty acid having 8 or more carbon atoms.

2. A preparation as claimed in claim 1, comprising 0.001–5% of azelastine hydrochloride, a hydrocarbon selected from the group consisting of white petrolatum, yellow petrolatum, and gelatinized hydrocarbon, a higher alcohol selected from the group consisting of stearyl alcohol, cetanol and cetosteryl alcohol, and a surfactant selected from the group consisting of polyoxyethylene hydrogenated castor oil, glycerol monostearate, polyoxyethylene lauryl ether, and cholesterol.

3. A preparation as claimed in claim 1, comprising 0.001–5% a zelastine hydrochloride, a hydrocarbon selected from the group consisting of white petrolatum, yellow petrolatum, and gelatinized hydrocarbon, a polyhydric alcohol selected from the group consisting of propylene glycol and polyethylene glycol, and a surfactant selected from the group consisting of polyoxyethylene hydrogenated castor oil, glycerol monostearate, polyoxyethylene lauryl ether, and cholesterol.

4. A preparation as claimed in claim 1, comprising white petrolatum, polyoxyethylene lauryl ether and propylene glycol.

5. A preparation as claimed in claim 1, comprising white petrolatum, yellow petrolatum, polyoxyethylene hydrogenated castor oil, glycerol monostearate, stearyl alcohol, and propylene glycol.

* * * * *